(12) United States Patent
Castellin et al.

(10) Patent No.: US 8,871,953 B2
(45) Date of Patent: Oct. 28, 2014

(54) PROCESS FOR THE PREPARATION OF OLOPATADINE

(75) Inventors: Andrea Castellin, Padua (IT); Clark Ferrari, Vicenza (IT); Marco Galvagni, Verona (IT)

(73) Assignee: F.I.S. Fabbrica Italiana Sintetici S.p.A., Alte di Montecchio Maggiore (IT)

( * ) Notice: Subject to any disclaimer, the term of this patent is extended or adjusted under 35 U.S.C. 154(b) by 626 days.

(21) Appl. No.: 12/990,442

(22) PCT Filed: Mar. 23, 2010

(86) PCT No.: PCT/EP2010/053783
§ 371 (c)(1),
(2), (4) Date: Nov. 18, 2010

(87) PCT Pub. No.: WO2010/121877
PCT Pub. Date: Oct. 28, 2010

(65) Prior Publication Data
US 2011/0065936 A1    Mar. 17, 2011

(30) Foreign Application Priority Data
Apr. 21, 2009    (IT) .............................. MI2009A0659

(51) Int. Cl.
*C07D 313/12*    (2006.01)
*C07D 313/06*    (2006.01)

(52) U.S. Cl.
CPC .................................. *C07D 313/12* (2013.01)
USPC ......................................................... 549/354

(58) Field of Classification Search
USPC ........................................................ 549/354
See application file for complete search history.

(56) References Cited

U.S. PATENT DOCUMENTS

| 4,082,850 | A  | * | 4/1978 | Lassman et al. | ............... | 514/450 |
| 2012/0004426 | A1 | * | 1/2012 | Guisasola et al. | ............ | 549/354 |

FOREIGN PATENT DOCUMENTS

| EP | 0 214 779 A1 | 3/1987 |
| EP | 0 235 796 A2 | 9/1987 |
| EP | 0 799 044 A2 | 10/1997 |
| WO | WO 96/39147 A2 | 12/1996 |
| WO | WO 2007/110761 A2 | 10/2007 |
| WO | WO 2007/119120 A2 | 10/2007 |

OTHER PUBLICATIONS

E. Ohshima, et al., "Synthesis and Antiallergic Activity of 11-(Aminoalkylidene)-6,11-dihydrodibenz[b,e]oxepin Derivatives." Journal of Medicinal Chemistry, vol. 35, No. 11, pp. 2074-2084, May 1, 1992.
Xue et al., "Study on the Synthetic Process of a Novel Anti-Allergic Agent Olopatadine Hydrochloride." Zhongguo Yaowu Huaxue Zazhi—Chinese Journal of Medicinal Chemistry, vol. 14, No. 6, pp. 363-364, 367, Jan. 1, 2004.
J. Prous et al., KW-4679, "(Z)-11-[3-(Dimethylamino)propylidene]-6,11-dihydrodibenz[b.e]oxepin-2-acetic acid hydrochloride", Drugs of the Future 1993, 18(9), pp. 794-798.

* cited by examiner

*Primary Examiner* — Sun Jae Yoo
(74) *Attorney, Agent, or Firm* — Dickstein Shapiro LLP

(57) ABSTRACT

The present invention relates to a novel process for the preparation of olopatadine hydrochloride starting from an advanced intermediate.

27 Claims, 4 Drawing Sheets

PROCESS FOR THE PREPARATION OF OLOPATADINE

The present invention relates to a novel process for the preparation of olopatadine hydrochloride.

DESCRIPTION OF THE KNOWN ART

Olopatadine hydrochloride, chemical name dibenz[b,e]oxepin-2-acetic acid, 11-[3-(dimethylamino) propylidene]-6,11-dihydro hydrochloride, (11Z), of formula (I)

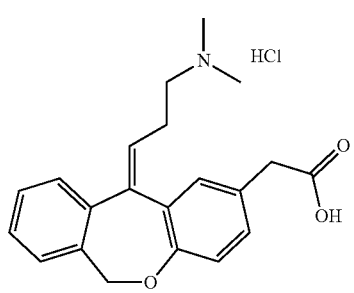

(I)

is a novel antihistamine marketed by Kyowa Hakko under the name of Allelock®. In particular, olopatadine is selective for histamine H1 receptors, predominantly localised in the bronchi, the cardiovascular system, the central nervous system and the intestine. As a formulation for oral administration, it is used in the oral treatment of the symptoms of allergic rhinitis, urticaria and dermatitis.

Both ophthalmic (Patanol®) (Pataday® or Patanol Plus®) and nasal spray (Patanase®) formulations are known.

On the other hand, its use as an anti-asthmatic is still in phase-II clinical development.

Olopatadine has first been described by GlaxoSmithKline (EP 214779) and subsequently by Kyowa (EP 235796), while its use in the treatment of conjunctivitis has been described by Alcon and Kyowa (EP 799044).

Regarding its preparation, the synthetic processes described in the product patent use isoxepac (or dibenz[b,e] oxepin-2-acetic acid, 6,11-dihydro-11-oxo) as an advanced intermediate. However, the known processes for the preparation of olopatadine consisting of the preparation of isoxepac have the drawback of giving a limited yield of final product. In addition, the product obtained is unsatisfactory in terms of purity, thus making the process for the attainment of a pharmaceutically acceptable active substance longer, more complex and more costly.

The originator states in the Journal of Medicinal Chemistry, 1992, 35, pages 2074-2084 that the attempts to prepare Olopatadine esters and analogs (compounds 37-40) employing the same Wittig reaction conditions employed starting from Isoxepac, but starting from Isoxepac esters and analogs, resulted in the recovery of the starting materials that means no reaction between the substrates.

Figure 1:
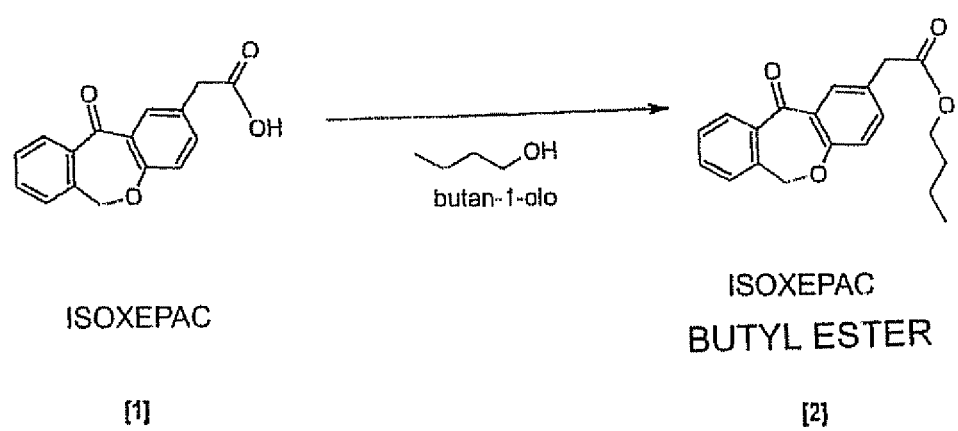
FIGS. 1 and 2 show the process for the preparation of olopatadine and its hydrochloride salt according to the present invention.
Figure 2:
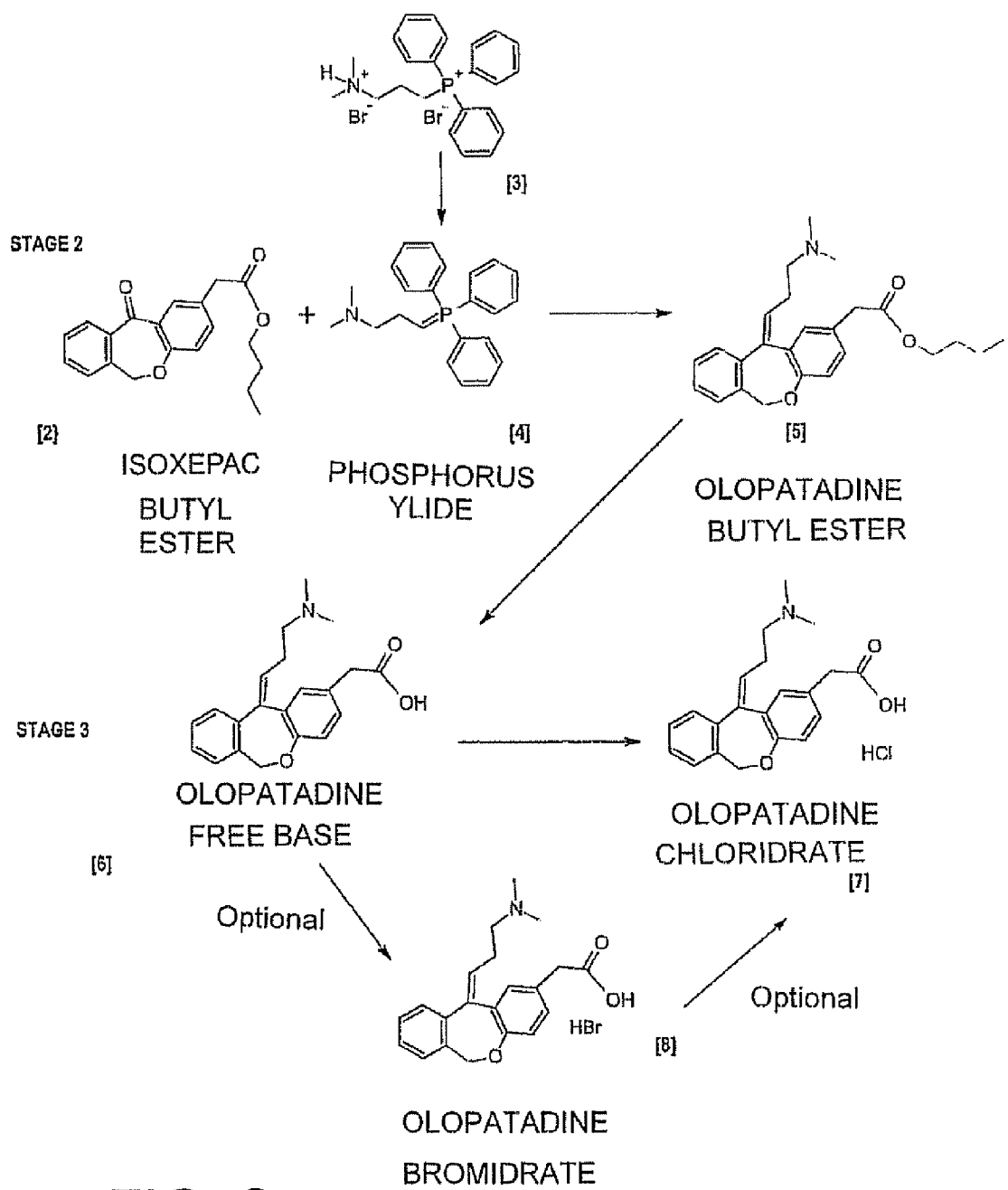

One of the aims of the present invention is thus to describe a process as reported in the schemes of FIGS. 1 and 2 for the preparation of olopatadine and the hydrochloride salt thereof, with higher yields than the already known processes and with a higher degree of purity.

In addition to this, the process described allows the attainment of a stereoisomeric ratio that is unexpectedly and advantageously in favour of the pharmaceutical active substance, having configuration (Z).

In particular, the invention concerns a process for the preparation of olopatadine comprising the preparation of the intermediate of formula (V)

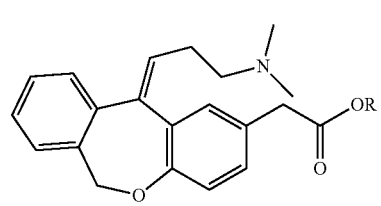

(V)

wherein R is a linear or branched C1-C4 saturated alkyl, comprising the steps of:
a) transforming isoxepac of formula

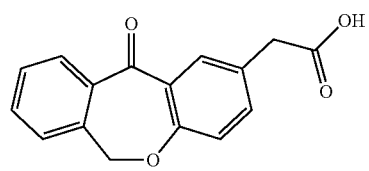

(IV)

into an ester of formula (IVa)

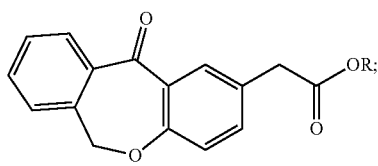

(IVa)

b) transforming the isoxepac ester (IVa) obtained from step a) into the compound of formula (V) by means of a Wittig reaction;
c) transforming the compound of formula (V) into olopatadine free-base.

More in detail, the present invention concerns a process for the preparation of olopatadine and the hydrochloride salt thereof, comprising the preparation of the olopatadine ester of formula V:

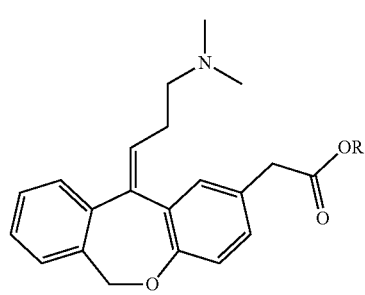

(V)

wherein R is a linear or branched C1-C4 saturated alkyl.

In particular, the process comprises a first step including the preparation of the isoxepac ester of formula (IVa) through the esterification of isoxepac (IV) with an alcohol R—OH in an acidic environment, wherein R is a linear or branched C1-C4 saturated alkyl, in accordance with Scheme 1 here below.

Scheme 1.

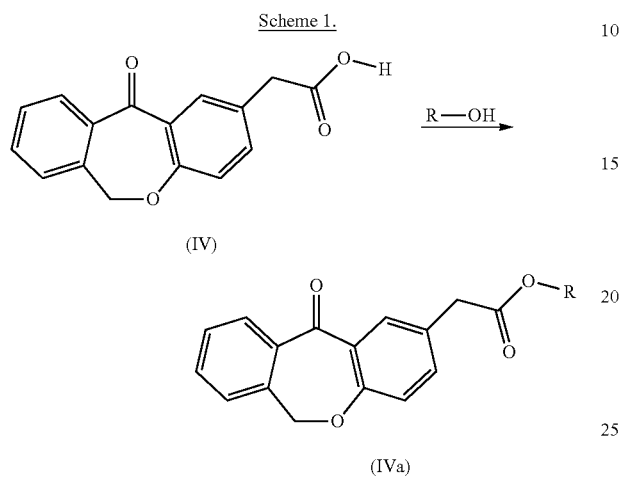

In one embodiment, having obtained the ester (IVa), this is purified by means of the addition of carbon then appropriately filtered, and then washed with a linear or branched C1-C4 saturated alcohol or, preferably, with the reaction alcohol, crystallised, and the crystals thus obtained dried at room temperature under vacuum.

In the second step of the process according to the present invention, the isoxepac ester (IVa) is made to react with a suitable phosphorus ylide by means of a Wittig reaction in an appropriate solvent, and the compound thus obtained subsequently treated in a basic environment to give the olopatadine ester (V) according to Scheme 2 below.

Scheme 2

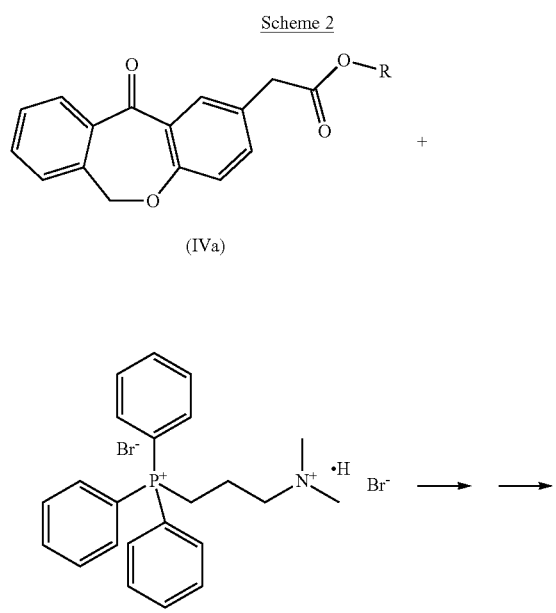

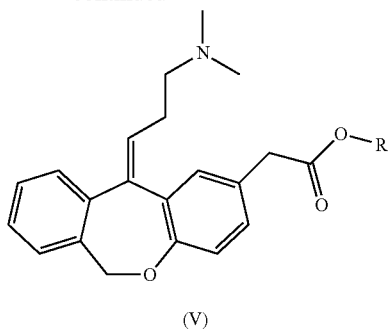

(V)

In one embodiment, on completion of the reaction, the mixture is chilled and purified water and sodium hydroxide added until the pH is basic, in order to obtain hydrolysis of the olopatadine ester, and then olopatadine as free base. Alternatively, hydrolysis may be obtained with other inorganic bases, such as for example potassium hydroxide.

Optionally, Olopatadine free-base can be converted into a Olopatadine salt, such as, Olopatadine hydrobromide, by the subsequent acid treatment from pH 12-14 to pH 3.3-3.4 to give a salt of olopatadine. This is followed by crystallisation from acetone and congeneric compounds thereof and linear or branched C1-C4 saturated alcohols, preferably n-butanol, or with the reaction alcohol, and drying the crude olopatadine salt crystals under reduced pressure.

Purification is subsequently performed by dissolution into a mixture consisting of purified water and acetone or congeneric compounds thereof and a linear or branched C1-C4 saturated alcohol, preferably n-butanol, or the reaction alcohol, followed by chilling. The pure olopatadine salt crystals thus obtained are washed once more with linear or branched C1-C4 saturated alcohol, preferably n-butanol, or with the reaction alcohol, previously chilled to 0-5° C., in acetone or congeneric compounds thereof, and then dried under reduced pressure.

According to a further embodiment, olopatadine free-base is obtained, for example, following treatment of the crystals in a solution of purified water containing acetone, to which acticarbon and toluene are then added. Sodium hydroxide is then added to the aqueous phase thus obtained until the pH is >12.

If the optional step of converting the olopatadine free-base above referred into an olopatadine salt like olopatadine hydrobromide is not carried out, hydrochloric acid is added to the aqueous phase containing the olopatadine free-base, until the pH is between 2.5 and 3.0.

The aqueous phase is washed 3 times with toluene to remove organic impurities, then sodium hydroxide 30% is added to bring the pH from 6.8 to 7.2 and then part of acetone is distilled. The resulting suspension is then cooled, filtered, and the crystals obtained washed with purified water and then dried under vacuum. Olopatadine free-base can be conveniently re-crystallised with about 4 volumes of dimethylformamide.

In the final step of the process of the present invention, olopatadine free-base is treated with hydrochloric acid in acetone to give olopatadine hydrochloride, in accordance with Scheme 3 below.

Scheme 3

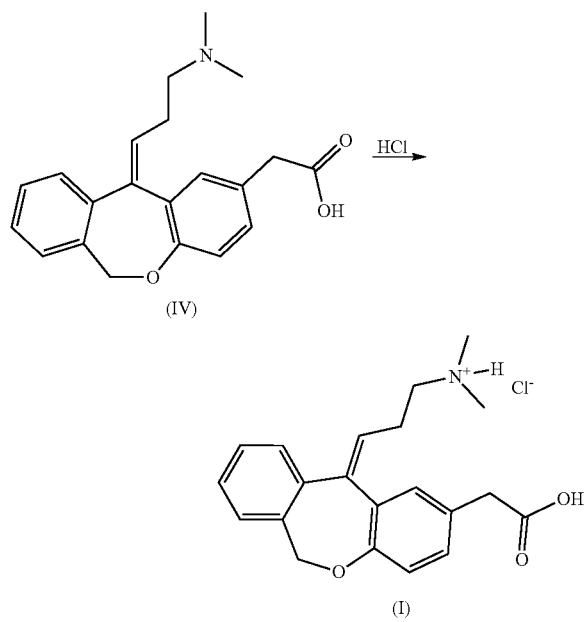

The obtained final product is filtered, washed once more with acetone and subsequently dried under reduced pressure.

In the process of the present invention, the starting compound, i.e. isoxepac, is commercially available or, alternatively, may be prepared in accordance with known methods available in the literature.

In turn, the isoxepac (IV) esterification reaction is conducted in accordance with methods known to those skilled in the art and in the presence of an acid, selected for example, from sulphuric acid or p-toluenesulphonic acid (see, for example, March's Advanced Organic Chemistry, 6$^{th}$ Ed., page 1414 or as described in U.S. Pat. No. 4,082,850, the content of which is incorporated herein by way of reference).

As already mentioned, the alcohols used in the esterification reaction are alcohols of formula R—OH, wherein R is a linear or branched C1-C4 saturated alkyl, and are preferably methanol, isopropanol and normal-butanol, the latter being most preferred, thus giving the isoxepac butyl ester of formula IVb.

(IVb)

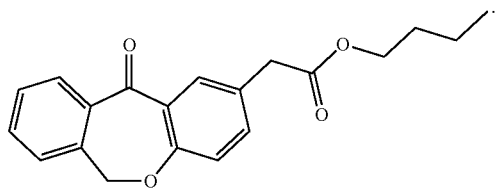

With regard to the Wittig reaction between the phosphorus ylide and the isoxepac ester (IVa), this is performed using 3-dimethylaminopropyltriphenyl-phosphonium hydrobromide, the formula of which is reported below,

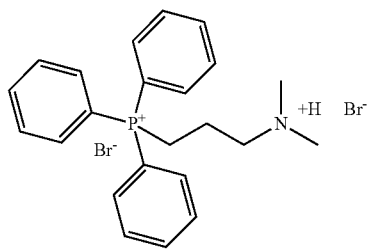

which is a commercially available product, alternatively, obtainable from dimethylamine and (3-bromopropyl)triphenylphosphonium bromide, the latter of which may be purchased or may be prepared from 1,3-dibromopropane and triphenylphosphine, in accordance with Scheme 4 below.

Scheme 4

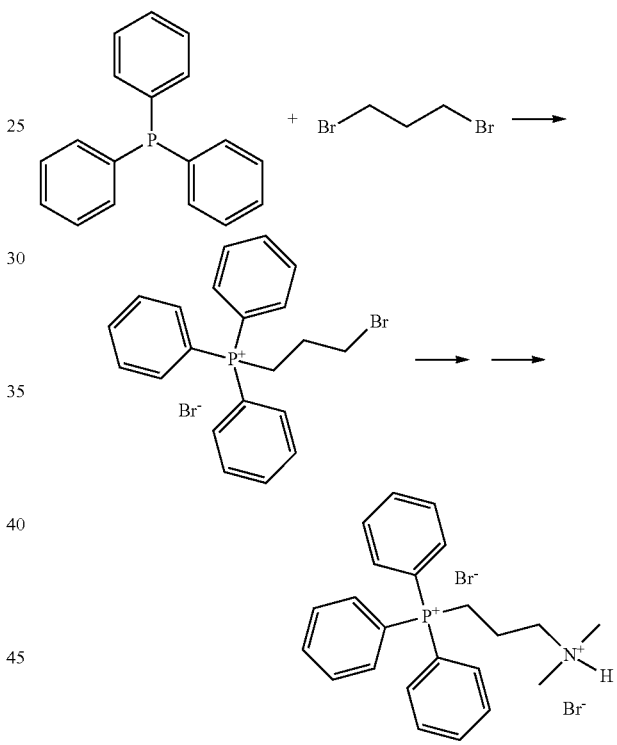

In particular, a phosphorus ylide/isoxepac ester equivalent ratio of approx. 1.5, preferably 1.2, is used for this reaction. Furthermore, the Wittig reaction is preferably and advantageously performed in a suitable solvent, such as for example, methyltetrahydrofuran or other similar ethers, such as, for example, terbutylether, diisopropylether or tetrahydrofuran. Alternatively, mixtures of the above-mentioned ethers with aliphatic or aromatic hydrocarbons may be used.

On the other hand, with regard to the salification of the olopatadine obtained from the hydrolysis of olopatadine ester (V), this is advantageously obtained by treatment with hydrobromic acid, thus giving the hydrobromide salt of olopatadine, or with hydrochloric acid, thus giving the hydrochloride salt of olopatadine (see, for example, the diagram shown in FIGS. 1 and 2).

It is another aspect of the present invention the content of the bromide ions in the final Olopatadine hydrochloride product.

Bromide ions represent a process impurity; they are responsible for appetite loss, nausea/emesis, lethargy, propensity to sleep during the daytime and headache; therefore it is convenient to reduce to the lowest extent the content of such ion impurity into the final product.

The bromide ion content into olopatadine hydrochloride can be quantified by ion chromatography (IC) according the method enclosed in Example 6.

The patent document WO 2007/119120 discloses a different process for the preparation of Olopatadine hydrochloride which contains less than 1000 ppm of bromide ions. The examples show a bromide content of 600-800 ppm. The bromide content in the pharmaceutical product, according our analysis, is around 1100-1150 ppm.

The process according to the present invention provides olopatadine hydrochloride having a bromide content lower than 300 ppm and preferably lower than 30 ppm, which is the detection limit of the IC method enclosed in the examples.

Kilolab samples prepared according to the process of the invention show not to contain bromide ions (always under 30 ppm, often 0 ppm).

Accordingly, another aspect of the invention is represented by the purity of the final product in terms of process organic impurities content. The process of the invention allows the preparation of Olopatadine hydrochloride having an HPLC purity equal or higher than 99.90% (Area %), having each single impurity lower than 0.05% (HPLC Area %) (see the European Pharmacopoeia, General Chapter <2034>) and HPLC assay (% w/w) comprised in the range between 99 and 101%.

During the process development, it was noted that a process impurity was particularly difficult to remove from the product, thus not allowing to obtain a product with all impurities under 0.05% (HPLC Area %).

Figure 3:
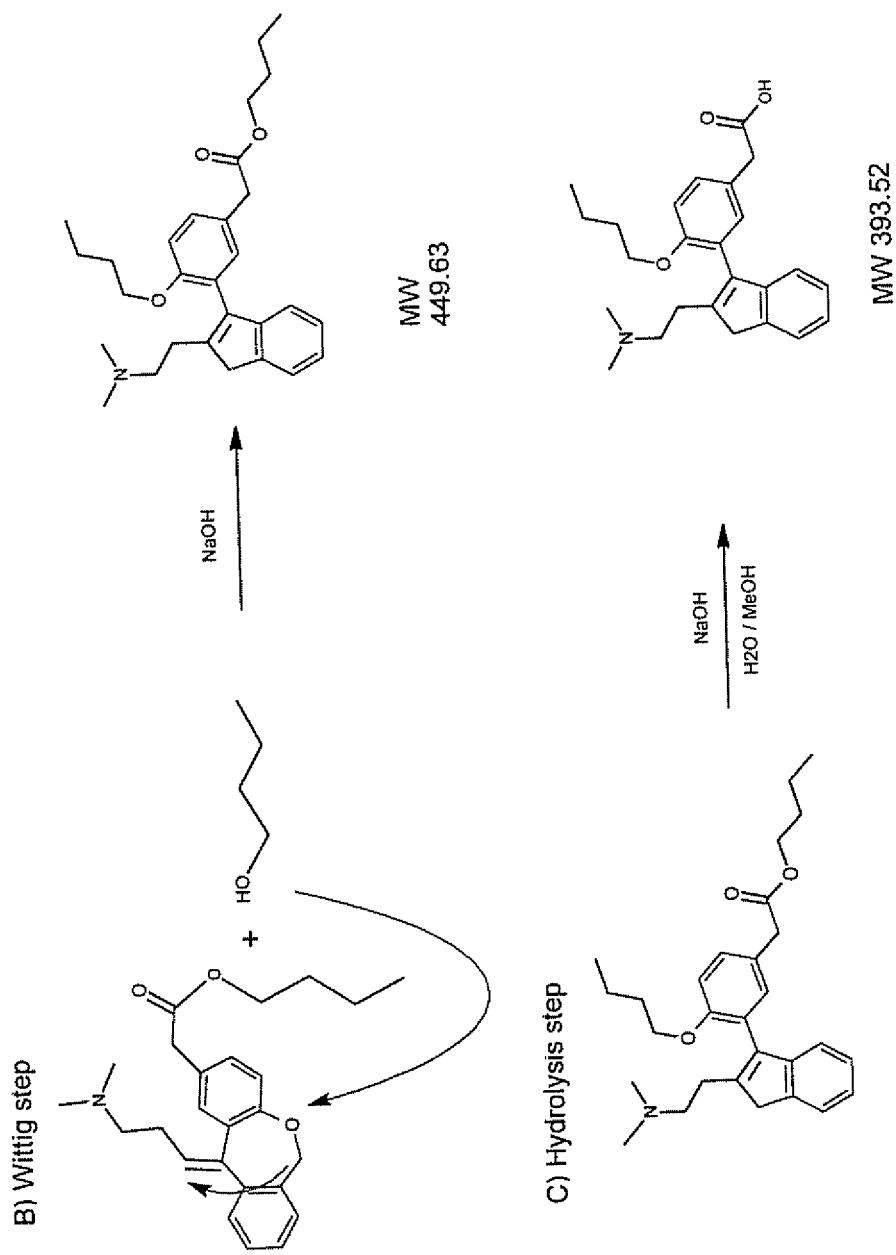
FIGS. 3 and 4 show the formation mechanisms of process impurities as disclosed in the following description.

A LC/MS and NMR study has elucidated the structure of the impurity and has clarified the mechanism of formation of the impurity and its precursor according the scheme of FIG. 3.

The n-butyl ester of the impurity (3-{2-[2-(dimethylamino) ethyl]-1H-inden-3-yl}-4-n-butyloxyphenyl) acetic acid is therefore generated during the Wittig reaction step and then it is hydrolysed to the free-acid form during the step of hydrolysis of oloptadine esters to olopatadine.

It was surprisingly found that inverting the order of addition of the solution containing the phosphorous ylide to a solution comprising isoxepac ester of formula (IVa) instead of adding the solution containing the Isoxapac ester to solution containing the phosphorous ylide, the amount of the impurity (3-{2-[2-(dimethylamino)ethyl]-1H-inden-3-yl}-4-n-butyloxyphenyl)acetic acid in olopatine hydrochloride becomes lower than 0.05% (HPLC Area %).

The addition of the solution of phosphorous ylide is performed in a range of temperature comprised between 10° C. and 60° C. and in a time comprised between 30 minutes and 120 minutes. Preferably, such addition is performed at 30-50° C. in 60 minutes, more preferably at 38-42° C. in 60 minutes.

Figure 4:
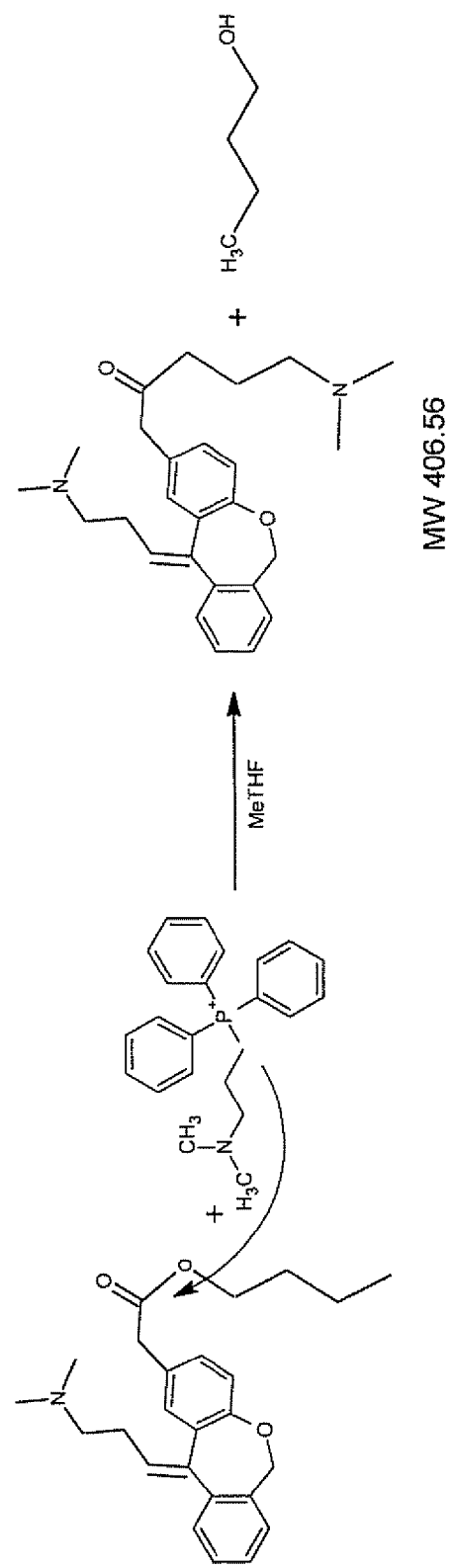

Moreover, said reversed addition allows to improve the yield of the process avoiding the side-reaction exemplified in the scheme of FIG. 4.

Those skilled in the art may appreciate how the process of the present invention allows the attainment of both the free olopatadine and the hydrobromide or hydrochloride salt thereof, with high yield and high purity, thanks also to the possible isolation of the olopatadine ester intermediate, preferably the butyl ester of olopatadine and more preferably the normal-butyl ester, making it possible to reduce or even exclude the presence of secondary products, and hence impurities in the final product, thus giving a pharmaceutical active substance of pharmaceutically acceptable grade.

Furthermore, the Wittig reaction itself, requiring a less phosphorus ylide and sodium hydride amounts, allows significant cost savings.

Hence, it is evident how the process of the present invention is particularly advantageous for application at both the laboratory and industrial scale.

The process of the invention provides olopatadine hydrochloride bromide free, having crystalline form A and a pharmaceutically acceptable grade. Olopatadine hydrochloride obtained according to the process of the invention can be conveniently formulated into pharmaceutical compositions comprising at least one pharmaceutically acceptable excipient to be used as a medicament, particularly as an antihistaminic or antiallergic medicament.

EXAMPLE 1 a) Preparation of Isoxepac Butyl Ester

In a 3 l flask equipped with a thermometer, stirrer, condenser and Dean-Stark apparatus, add 100 g of Isoxepac (11-oxo-6,11-dihydrodibenzo[b,e]oxepin-2-yl)acetic acid), 1600 ml of n-butanol, 0.2 ml of sulphuric acid. Heat up to boiling temperature (approx. 115° C.) and continue stirring at said temperature for at least 2 hours.

After stirring for 2 hours, distil 500 ml of solvent at atmospheric pressure. Chill to T=20/25° C., add 10 g of carbon to the reaction mixture, stir at T=20/25° C. for 10 minutes and filter through dicalite, washing with 100 ml of n-butanol. Concentrate under vacuum to give an oily residue and add 350 ml of heptane isomers. Chill to T=−15/−20° C. so as to crystallise the product. Stir at T=−15/−20° C. for 1 hour and filter, washing the crystals obtained with 90 ml of heptane isomers at T=−15/−20° C. Dry the product under vacuum at a temperature of 25° C. for at least 8 hours. Yield: 112.5 g, 93%; Titre by HPLC >99.5%, Purity by HPLC>99.5%

NMR (DMSO $d_6$): 0.84 (s, 3H), 1.29 (dd,2H), 1.53 (dd, 2H), 3.71 (d,2H), 4.03 (dd,2H), 5.28 (d,2H), 7.07 (d,1H), 7.54 (m, 4H),7.78 (s,1H), 8.00 (s,1H)).

b) Preparation of Olopatadine Hydrobromide (Crude)

Load 29.6 g of 60% sodium hydride in mineral oil (4.0 eq.), 164.85 g of (3-dimethylaminopropyl)triphenylphosphine bromide-HBr (1.75 eq.) and 360 ml of THF (6 V) into a flask. Stir at T=0/5° C. for 30 minutes, then heat the mixture slowly to T=60° C. and stir at said temperature for 3 hours. Chill to a temperature of 0-5° C. and add a mixture consisting of 60 g of isoxepac butyl ester in 210 ml of THF over molecular sieves (3.5 V). Heat the reaction mixture to T=27-30° C. and stir at said temperature for at least 15 hours.

Having verified that the reaction has gone to completion, chill to T=0-5° C. and add 80 ml of purified water followed by 35 ml of 30% NaOH.

Heat the reaction mixture to T=55-60° C. and stir at said temperature for at least 4 hours. Chill to T=20-25° C. and add 300 ml of purified water. Ensure that the pH of the mixture is basic and concentrate under vacuum to obtain 600 ml of solvent. On completion of the distillation process, add 240 ml of purified water and 360 ml of toluene. Stir for at least 20 minutes at T=20-25° C. and then separate the phases, discarding the organic phase. Wash the aqueous phase containing the product once more with 360 ml of toluene. Then wash the aqueous phase with 3×360 ml of methylene chloride, taking care to always preserve the aqueous phase. Distil under maximum vacuum and Tmax of 70° C. until 200 ml of distillate is collected. Add a mixture of isopropanol/methyl THF, prepared using 500 ml of methyl THF and 100 ml of isopropanol, to the aqueous phase. Adjust the pH of the aqueous phase from 12-14 to between 3.3 and 3.4, maintaining T=20-25° C., by adding 70 ml of 60% hydrobromic acid solution. Stir for at least 20 minutes at T=20-25° C. and then separate the phases, preserving the organic phase. Extract the aqueous phase twice more with a mixture consisting of 500 ml of methyl THF and 100 ml of isopropanol. After having combined the organic phases, concentrate the solution under vacuum to give an oily residue. Take up the oil in 500 ml of n-butanol and then concentrate under vacuum once more (bath Tmax=45° C.) to obtain an oil once more and so as to have azeotropically removed all the water. Then add 480 ml of n-butanol to the obtained oil. Heat the mixture to dissolve the product (T=70-80° C.). Chill to T=50° C. and optionally spike with olopatadine-HBr, so as to promote crystallisation. Then chill to T=20-25° C. and stir at said temperature for at least 15 hours. Filter the product, taking care to wash the crystals with 96 ml of n-butanol. Dry under reduced pressure at T=80° C. for at least 12 hours.

Yield: 47 g, 61%; Titre by HPLC>90%, Purity by HPLC>95%

NMR (DMSO $d_6$): 2.74 (s, 6H), 3.39 (br, 6H), 5.19 (br, 2H), 5.61 (t, 1H), 6.76 (d, 1H), 7.04-7.13 (m, 2H), 7.24-7.43 (m,4H), 10.80 (s, 1H), 12.34 (s,1H)).

c) Preparation of Olopatadine Hydrobromide RIXX

Load 45 g of crude olopatadine-HBr, 270 ml of n-butanol and 4.5 ml of purified water into a flask. Heat the mixture until the product is dissolved (T=75-80° C.). Then chill slowly to T=0-5° C. and stir at said temperature for 1 hour. Filter and wash the crystals obtained with 65 ml of n-butanol, previously chilled to T=0-5° C. Dry under reduced pressure at T=80° C. for at least 8 hours.

Yield: 36 g, 80%; Titre by HPLC>98%, Purity by HPLC>95%.

NMR (DMSO $d_6$): 2.74 (s, 6H), 3.39 (br, 6H), 5.19 (br, 2H), 5.61 (t, 1H), 6.76 (d, 1H), 7.04-7.13 (m, 2H), 7.24-7.43 (m,4H), 10.80 (s, 1H), 12.34 (s,1H)).

d) Preparation of Olopatadine Free-Base

Load 100 g of purified olopatadine-HBr, 1600 ml of purified water (16 V) and 650 ml of acetone (6.5 V) into a flask. Heat the mixture slowly to T=35-45° C. until the product is dissolved. Add 7.5 g of acticarbon to the mixture, and stir while maintaining the temperature at T=35-45° C. for 15 minutes. Filter the carbon over a panel of dicalite, taking care to wash the activated carbon with a mixture containing 75 ml of purified water (0.75 V) and 40 ml of acetone (0.4 V) previously warmed to T=35-45° C. Then add 600 ml of toluene (6 V) to the filtered solution, maintained at T=35/45° C., and stir for at least 10 minutes at T=35-45° C. prior to the separation of the phases. Discard the organic phase.

Chill the aqueous phase to a temperature of T=20-25° C. and add 30% NaOH to achieve a pH>12. Then add 600 ml of toluene (6 V) to the solution obtained, maintaining T=20-25° C., stir for 10 minutes and then separate the phases, discarding the organic phase.

Then, maintaining T=20-25° C., add 30% HCl to the aqueous phase obtained in order to obtain a pH of between 6.8 and 7.2. Distil under vacuum, maintaining an internal Tmax below 50° C., to a residual volume of 850 ml, so as to eliminate all the acetone present and crystallise the product. Then chill the suspension to T=15-20° C. Filter the product and wash with 300 ml of purified water (3 volumes). Dry under reduced pressure at T=50° C. for at least 12 hours.

Yield: 73 g, 90%; Titre by HPLC>99.5%, Purity by HPLC>99.5% (Area %);

NMR (DMSO $d_6$): 2.20 (s, 6H), 2.55 (m, 4H), 3.40 (s, 2H), 5.18 (br, 2H), 5.63 (t, 1H), 6.75 (d, 1H), 7.04-7.13 (m, 2H), 7.24-7.43 (m, 4H).

e) Preparation of Olopatadine Hydrochloride

Load 100 g of olopatadine free-base and 140 ml of purified water (1.4 V) into a flask. Maintaining T=20-25° C., add 58.2 ml of 30% HCl (2.0 eq.) dropwise until the free-base is dissolved, then add 2100 ml of acetone (21 V) to the mixture, maintaining T=20-25° C. Stir at T=20-25° C. for at least 1 hour, chill to T=0-5° C. and stir at said temperature for at least 2 hours. Filter the product and wash with 525 ml of acetone (5.25 V). Dry under reduced pressure at T=50° C. for at least 12 hours.

Yield: 70 g, 63%; Titre by HPLC>99.9%, Purity by HPLC>99.8%; (DMSO $d_6$): 2.70 (s, 6H), 2.79 (t, 2H), 3.24 (t, 2H), 3.54 (s, 2H), 5.18 (br, 2H), 5.63 (t, 1H), 6.77 (d, 1H), 7.04-7.13 (m, 2H), 7.24-7.43 (m, 4H), 10.80 (s, 1H), 12.34 (s, 1H)).

m.p. (DSC Onset): 253° C. (polymorphic form A).

A compound of crystalline form A and pharmaceutically acceptable grade is thus obtained.

EXAMPLE 2

The process according to Example 1 is repeated, but proceeding to isolate the olopatadine butyl ester intermediate in step b), as described below.

Load 29.6 g of 60% sodium hydride in mineral oil (4.0 eq.), 164.85 g of (3-dimethylaminopropyl) triphenylphosphine bromide-HBr (1.75 eq.) and 360 ml of THF (6 V) into a flask. Stir at T=0/5° C. for 30 minutes and then heat the mixture slowly to T=60° C. and stir at said temperature for 3 hours. Chill to a temperature of 0-5° C. and add a mixture consisting of 60 g of isoxepac butyl ester in 210 ml of THF over molecular sieves (3.5 V). Heat the reaction mixture to T=27-30° C. and stir at said temperature for at least 15 hours.

Having verified that the reaction has completed, chill to T=0-5° C., add 80 ml of purified water and then neutralise by adding 32% HCl until reaching pH 7.

Distil under vacuum until all the THF (at least 550 ml) is collected. Add 400 ml of toluene and 200 ml of purified water. Stir and then separate the phases.

Add 300 ml of heptane to the toluene phase and stir for at least 1 hour. Filter the phosphines obtained and concentrate the organic phase containing the olopatadine butyl ester isomers.

Collect the oil thus obtained with 150 ml of n-butanol, chill to T=−10/−15° C. and stir for 1 hour until the product has crystallised. Filter and wash with 20 ml of n-butanol and chill to T=−15° C.

The olopatadine butyl ester thus obtained has the following NMR spectrum:

(DMSO $d_6$): 0.90 (t, 3H), 1.32 (sest., 2H), 1.60 (quint., 2H), 2.23 (s, 6H), 2.45 (t, 2H), 2.6 (q., 2H), 3.51 (s, 2H), 4.08 (t, 2H), 5.40 (sb, 2H), 5.7 (t, 1H), 6.80 (d, 1H), 7.06 (dd, 2H), 7.30 (m, 4H).

The olopatadine butyl ester is then treated with sodium hydroxide followed by hydrobromic acid to give the olopatadine hydrobromide salt in crude form, to be purified or to be used for subsequent process steps (steps c)-e)).

EXAMPLE 3

Preparation of Olopatadine Free Base

A RBF is charged with 19.6 g 60% sodium hydride in mineral oil (2.76 mol. equivs.), 117.7 g of (3-dimethylaminopropyl)triphenylphosphin Bromide hydrobromide (1.3 mol. equivs) and 300 mL of Methyl-THF on molecular sieves previously degassed by nitrogen bubbling.

Stir at T=0/5° C. for 30 minutes and then heat slowly the mixture at T=40° C. in about 1 hour.

Heat the mixture at reflux temperature (ca. 80-82° C.) in about 30 minutes and stir for at least 6 hours.

Cool down at T=38-42° C. in about 30 minutes and keep at the temperature for one hour.

In about 60 minutes and keeping the temperature at T=38/42° C. add the above prepared solution to a solution consisting in 60 g of Isoxepac butyl ester in 210 mL of Methyl-THF on molecular sieves previously degassed by nitrogen bubbling.

Stir the solution for at least 2 hours at T=38-42° C. When the reaction is considered completed, the mixture is cooled at T=0/5° C. in about 1 hour and added in about 1 hour with 250 mL of purified water. The mixture is then heated at T=10/15° C. and the phases are separated.

The organic phase is washed twice with a solution of 35 g of sodium chloride in 220 mL of purified water each time. The organic phase containing Olopatadine normal-butyl ester is distilled at T max=50° C. under vacuum to remove the solvent, then the residue is added with 810 mL of methanol and 450 mL of purified water.

The mixture is cooled at T=5/10° C. and a solution of 8.8 g of KOH and 79.5 mL of purified water is dropped keeping T at 5/10° C. in about 30 minutes. The mixture is heated at T=60/70° C. in about 30 minutes and kept at this temperature for at least 3 hours. When the reaction of ester hydrolysis is completed the mixture is cooled down at T=20-25° C. in about 30 minutes then, keeping Tmax=65° C., the mixture is distilled until 900 mL of solvent are collected. A solution of 7.4 mL of NaOH 30% (w/w) and 450 mL of Toluene is added to the mixture and, after stirring for at least 20 minutes at T=20/25° C., the phases are separated. The aqueous phase is extracted three time with 360 mL of toluene each time at T=20/25° C., then add 250 mL of acetone and hydrochloric acid 32% (w/w) (ca. 35 mL) to reach pH=2.5-3.0. Add to the mixture 3 g of Acticarbon SA189 and stir for at least 15 minutes at T=20-25° C. Filter the mixture on celite washing the filter with a mixture of 40 mL of purified water and 18 mL of acetone. Add to the mixture 250 mL of toluene, heat at T=35-45° C. and separate the phases. Add to the aqueous phase NaOH aq. 30% (ca.18.5 mL) to reach pH=6.8-7.2. The mixture is concentrated under vacuum at T max.=60° C. until the final volume of 280 mL then, cool down at T=20/25° C. and stir at this temperature for at least 6 hours to promote the precipitation of Olopatadine free base. (If after 2 hours the product does not crystallize, seed the mixture with Olopatadine free base). The slurry is cooled at T=15-20° C., stirred for at least 1 hour, filtered and the cake is washed with 80 mL of purified water. The product Oloptadina free base is dried at T=60° C. for at least 8 hours obtaining 28.8 g (molar yield=46.1%).

EXAMPLE 4

Re-Crystallization of Olopatadine Free Base.

A RBF is charged with 50 g of Oloptadine free base (of Example 3) and 200 mL of DMF (dimethylformamide) and heated at T=95-105° C. until dissolution of the product. Cool down the solution at T=0-5° C. in about 2 hours and stir for 3 hours. The slurry is filtered and the product is washed with 85 mL of DMF at T=0/5° C. The product is dried at T=60° C. for at least 8 hours obtaining 45.0 g (yield=90%).

EXAMPLE 5

A RBF is charged with 100 g of Olopatadine free base (of Example 4), 60 mL of purified water, 100 mL of acetone and, keeping T=20-25° C., add in 10/15 minutes 44 mL of hydrochloric acid 32% (w/w). Keeping T=20-25° C., add to the mixture in about 30 minutes 1800 mL of acetone. Heat the slurry at reflux (T about 60° C.) in about 30 minutes and stir for at least 30 minutes. Cool down the slurry at T=20-25° C. and stir for at least 1 hour then cool at T=0-5° C. in about 1 hour and stir for at least 2 hours. The slurry is filtered and the cake is washed with 400 mL of acetone previously cooled at T=0-5° C. The product Olopatadine hydrochloride is dried under vacuum at T=50° C. for at least 6 hours obtaining 90.0 g (molar yield=81.2%). HPLC purity: 99.94% (Area %) and all impurities are lower than 0.05% (HPLC Area %) (according HPLC method of example 7). Bromide ion=not detected (0 ppm) (according to the IC method of Example 6). m.p.=253° C. (DSC Onset).

Olopatadine hydrochloride bromide free of crystalline form A and pharmaceutically acceptable grade is thus obtained.

EXAMPLE 6

Bromide Content-Ion Chromatography Method.
Instrument: Dionex ICS-1500 Ion Chromatography System;
Suppressor: AAES Anion Atlas electrolytic Suppressor;
Column: Ionpak AS 14°, 250×4 mm;
Pre-column: Ionpak AS 14°, 50×4 mm;
Column Temperature colonna: 30° C.;
Autosampler: AS 50 Autosampler;
Injection Volume: 25/L;
Mobile Phase: Buffer Na2CO3 8 mM e NaHCO3 1 mM in water;
Flow: 1.0 mL/min;
Detector: conductivity, ICS 1500 55 mA*;
Time of Analysis: ~20 minutes;
Solvent for analysis: water.

EXAMPLE 7

HPLC Method for the Determination of Olopatadine Hydrochloride Purity (Area %).
Chromatographic conditions:
Column: YMC ODS Aq 250×4.6 mm, 3 μm
Temp. column: 20° C.
Phase A: $HClO_4$ 0.1% in $H_2O$
Phase B: ACN

|  | Time (min) | % A | % B |
|---|---|---|---|
| Gradient: | 0 | 80 | 20 |
|  | 27 | 55 | 45 |
|  | 42 | 10 | 90 |
|  | 45 | 10 | 90 |

Equilibrium Time: 10 min.
Flow: 1.1 mL/min
Detector : UV 210 nm, bw 4 nm
Injection Volume: 5 μL
Diluent: $H_3PO_4$ 0.1% in $H_2O$ /ACN (8/2)
Time of analysis: 45 min

The invention claimed is:
1. A process for the preparation of olopatadine comprising the preparation of the intermediate of formula (V)

wherein R is methyl, ethyl, propyl, or butyl, comprising the steps of:
a) transforming isoxepac of formula (IV)

into an ester of formula (IVa)

(IVa)

b) transforming the isoxepac ester (IVa) obtained from step a) into the compound of formula (V) by means of a Wittig reaction; and
c) hydrolysing the compound of formula (V) to give olopatadine free-base,
wherein in step b) the isoxepac ester of formula (IVa) is made to react with an appropriate solution comprising phosphorus ylide in an appropriate solvent, in the presence of sodium hydride, to give the compound of formula (V), wherein R is as previously defined, and the solution comprising the phosphorus ylide in the appropriate solvent is added to the solution comprising the isoxepac ester of formula (IVa).

2. The process for the preparation of olopatadine according to claim 1, wherein step a) occurs in the presence of an alcohol of formula R—OH, wherein R is as previously defined, and a suitable acid catalyst.

3. The process for the preparation of olopatadine according to claim 2, wherein said acid catalyst is sulphuric acid or paratoluenesulphonic acid.

4. The process for the preparation of olopatadine according to claim 1, wherein R is normal-butyl.

5. The process for the preparation of olopatadine according to claim 1, wherein said phosphorus ylide is 3-dimethylaminopropyltriphenyl-phosphonium hydrobromide.

6. The process for the preparation of olopatadine hydrochloride according to claim 5, wherein said phosphorus ylide is used in a phosphorus ylide/isoxepac ester normality ratio of between 1 and 3.

7. The process for the preparation of olopatadine according to claim 1, wherein the solvent used is methyltetrahydrofuran, tetrahydrofuran or mixtures thereof with ethers, such as terbutylether or diisopropyl ether.

8. The process for the preparation of olopatadine according to claim 1, wherein the hydrolysis of step c) is obtained using sodium hydroxide.

9. The process for the preparation of olopatadine according to claim 1, further comprising the step of:
d) salifying the olopatadine free-base with an appropriate acid to give an olopatadine salt in crude form.

10. The process for the preparation of olopatadine according to claim 1, wherein the olopatadine ester (V) obtained in step b) is isolated as an intermediate.

11. The process according to claim 10, wherein said isolated intermediate is an olopatadine ester wherein R is normal-butyl.

12. The process according to claim 9, wherein the acid used for salification is added until a pH of approximately 3.3-3.4 is obtained.

13. The process according to claim 9, wherein the acid used for salification in step d) is hydrobromic acid or hydrochloric acid, giving the hydrobromide or hydrochloride salt of olopatadine respectively, in crude form.

14. The process according to claim 9, wherein the olopatadine salt obtained from step d) is subsequently purified by crystallisation from an appropriate solvent.

15. The process according to claim 14, wherein pure olopatadine salt is obtained by crystallisation from n-butanol.

16. The process according to claim 13, wherein the acid used for salification in step d) is hydrobromic acid and olopatadine hydrobromide salt is converted to olopatadine freebase by treatment with sodium hydroxide in an appropriate solvent.

17. The process according to claim 16, wherein sodium hydroxide is added until pH >12 is achieved.

18. The process according to claim 16, wherein said solvent is toluene.

19. The process according to claim 16, comprising the step of treating olopatadine free-base with hydrochloric acid in an appropriate solvent.

20. The process according to claim 19, wherein said solvent is acetone.

21. The process for the preparation of olopatadine according to claim 1, further comprising the step of re-crystallizing the Olopatadine free base with dimethylformamide.

22. The process according to claim 1, wherein the addition of the solution of phosphorous ylide is performed in a range of temperature comprised between 10° C. and 60° C. and in a period of time of between 30 minutes and 120 minutes.

23. A process for the preparation of olopatadine or its salts, comprising:
i) the preparation of the intermediate of formula (V)

(V)

wherein R is normal-butyl, comprising the steps of:
a) transforming isoxepac of formula

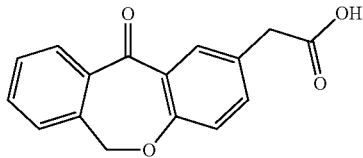

(IV)

into an ester of formula (IVa)

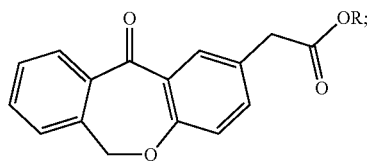

(IVa)

by means of esterification of isoxepac (IV) with an alcohol of formula R—OH; and,
b) transforming the isoxepac ester (IVa) obtained from step a) into the compound of formula (V) by means of a Wittig reaction;

ii) hydrolysing the compound of formula (V) to give olopatadine free-base; and,
iii) salifying the olopatadine free-base with an appropriate acid to give an olopatadine salt in crude form,
wherein in step b) the isoxepac ester of formula (IVa) is made to react with an appropriate phosphorus ylide in an appropriate solvent, in the presence of sodium hydride, to give the compound of formula (V), wherein R is normal-butyl, and the solution comprising the phosphorus ylide in the appropriate solvent is added to the solution comprising the isoxepac ester of formula (IVa).

24. The process for the preparation of olopatadine hydrochloride according to claim 5, wherein said phosphorus ylide is used in a phosphorus ylide/isoxepac ester normality ratio of 1.5.

25. The process for the preparation of olopatadine hydrochloride according to claim 7, wherein said phosphorus ylide is used in a phosphorus ylide/isoxepac ester normality ratio of 1.2.

26. The process according to claim 1, wherein the addition of the solution of phosphorous ylide is performed in a range of temperature comprised between 30° C. and 50° C. and in a period of time of 60 minutes.

27. The process according to claim 1, wherein the addition of the solution of phosphorous ylide is performed in a range of temperature comprised between 38° C. and 42° C. and in a period of time of 60 minutes.

* * * * *